United States Patent [19]

Altamura et al.

[11] Patent Number: 5,215,891
[45] Date of Patent: Jun. 1, 1993

[54] PROCESS FOR PREPARING PENEMS

[75] Inventors: Maria Altamura, Novara; Pietro Cesti, S. Martino di Trecate; Franco Francalanci, Novara; Marcello Marchi, Novara; Marco Foa', Novara; Stefano Cambiaghi, Pavia; Franco Dallatomasina, Segrate, all of Italy

[73] Assignee: Farmitalia Carlo Erba, Milan, Italy

[21] Appl. No.: 845,800

[22] Filed: Mar. 9, 1992

Related U.S. Application Data

[63] Continuation of Ser. No. 696,976, May 1, 1991, abandoned, which is a continuation of Ser. No. 106,809, Oct. 13, 1987, abandoned.

[30] Foreign Application Priority Data

Oct. 15, 1986 [GB] United Kingdom ............... 8624686

[51] Int. Cl.$^5$ .................... C12P 37/00; C12N 9/18
[52] U.S. Cl. ............................ 435/43; 435/44; 435/45; 435/41; 435/42
[58] Field of Search ............ 435/43, 44, 45, 196, 435/198, 185; 540/200, 201, 310, 357; 514/192, 199

[56] References Cited

U.S. PATENT DOCUMENTS

| | | | |
|---|---|---|---|
| 3,528,965 | 9/1970 | Cole et al. | 435/43 |
| 4,048,018 | 9/1977 | Coughlin et al. | 195/115 |
| 4,053,360 | 10/1977 | Bouzard et al. | 435/44 |
| 4,414,323 | 11/1983 | Masuda | 435/7.4 |

FOREIGN PATENT DOCUMENTS

| | | |
|---|---|---|
| 004736 | 1/1982 | European Pat. Off. |
| 2086897 | 5/1982 | United Kingdom |
| 2118181 | 10/1983 | United Kingdom |
| 2144743 | 3/1985 | United Kingdom |

OTHER PUBLICATIONS

Barrow, G. M. 1972. in: *General Chemistry*. Wadsworth Publ. Co., Belmont, Calif., pp. 600–602.
Grant, J. (ed.) 1969. in: *Hackh's Chemical Dictionary*. McGraw-Hill Book Co. New York. pp. 16, and 248.
Metzler, D. E. 1977. in: *Biochemistry. The Chemical Reactions of Living Cells*. Academic Press, New York, N.Y., p. 129.
Sigma Chemical Co. Catalog (1990) pp. 451, 653, 787, 950.
Webb, E. C. (ed.) 1984. in: *Enzyme Nomenclature 1984*. Academic Press. Inc., Orlando, Fla. pp. 270–273.
Windholz et al. (eds). 1983. in *The Merck Index*. Merck & Co., Rahway, N.J. p. 791.
Sigma Chemical Co. Catalog 1988. pp. 40–46.
Altamura et al., J. Chem. Soc. Perk. Trans. I (7):1225–1229 1989.

*Primary Examiner*—Christopher S. F. Low
*Attorney, Agent, or Firm*—Oblon, Spivak, McClelland, Maier & Neustadt

[57] ABSTRACT

A process for preparing a compound of formula I:

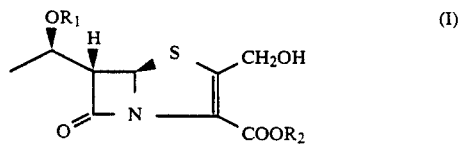

wherein $R_1$ represents a hydroxy protecting group and $R_2$ represents a carboxy protecting group, which comprises:
hydrolyzing a compound of formula II

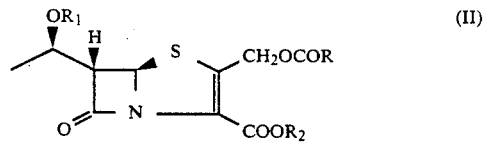

wherein $R_1$ and $R_2$ are as defined above and R represents an alkyl, alkenyl or phenylalkyl group having from 1 to 18 carbon atoms, in the presence of an enzyme capable of selectively hydrolyzing the ester group of the 2-substituent thereof.

6 Claims, No Drawings

PROCESS FOR PREPARING PENEMS

This application is a continuation of application Ser. No. 07.696,976, filed on May 1, 1991, which is a continuation of application Ser. No. 07/106,809 filed Oct. 13, 1987, now both abandoned.

BACKGROUND OF THE INVENTION

The present invention relates to a novel process for preparing 2-hydroxymethyl penems which are useful in the synthesis of penems having antibacterial activity. More particularly the invention relates to a process for the preparation of compounds of formula I:

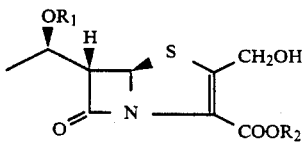

wherein $R_1$ represents a hydroxy protecting-group and $R_2$ represents a carboxy protecting group, which process comprises hydrolyzing a compound of formula II:

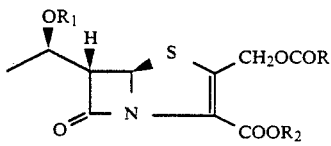

wherein $R_1$ and $R_2$ are as defined above and R represents an alkyl, alkenyl or phenylalkyl group having from 1 to 18 carbon atoms, by means of an enzyme capable of selectively hydrolysing the ester group of the 2-substituent thereof.

Suitable hydroxy protecting groups which $R_1$ may represent include p-nitrobenzyloxycarbonyl, 2,2,2,-trichloroethoxycarbonyl, trimethylsilyl, benzyl, p-bromophenacyl, triphenylmethyl and pyranyl groups. Preferred protecting groups are p-nitrobenzyloxycarbonyl, trimethylsilyl and pyranyl.

Suitable carboxy protecting groups which $R_2$ may represents include (a) alkyl groups having from 1 to 6 carbon atoms, (b) haloalkyl groups having from 1 to 6 carbon atoms, (c) alkenyl groups having from 2 to 4 carbon atoms, (d) optionally substituted aryl groups, (e) optionally substituted aralkyl groups, the alkyl part thereof has from 1 to 6 carbon atoms, and (f) aryloxyalkyl groups. Examples of these groups are: (a) methyl, ethyl and t-butyl, (b) 2,2,2-trichloroethyl, (c) allyl, (d) phenyl and p-nitrophenyl, (e) benzyl, p-nitrobenzyl, p-methoxybenzyl, diphenylmethyl and di-(o-nitrophenyl)-methyl and (f) phenoxymethyl. Other carboxy protecting groups include acetonyl and trimethylsilyl groups. Still other protecting groups are residues which are known to be hydrolyzed in vivo and which have favorable pharmacokinetic properties such as acetoxymethyl, pivaloyloxymethyl and phthalidyl groups. The preferred carboxy protecting groups are allyl, benzyl and p-nitrobenzyl groups.

Suitable alkyl groups which R may represent include methyl, ethyl, propyl, butyl, pentyl and hexyl. Suitable alkenyl groups include allyl, propenyl, butenyl. Suitable phenylalkyl groups include benzyl and phenethyl.

As stated above, compounds of formula I may be converted into known antibacterial agents, as in detail explained and claimed in our published U.K. Patent Application GB 2111496-A and GB 2118181-A. These known antibacterial agents, named penems, are described for example in British Patent Specifications 2043639-B, 2097786 B and in the published European Application 0167100-A.

As described in the above cited prior art, the compounds of formula I are prepared by chemical selective hydrolysis of compounds of formula III:

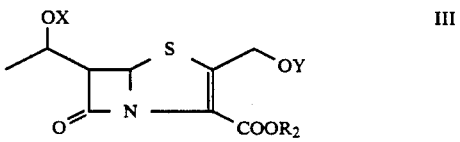

wherein $R_2$ is as defined above, and X and Y are two different silyl derivatives such as t-butyldimethyl silyl and t-butyldiphenylsilyl groups respectively, in the presence of tetraalkylammonium fluoride.

The synthesis of compounds III and said selective removal of protecting group Y require expensive reagents and long reaction times which are not suitable for industrial large scale preparation of penems. The present invention provides a simple process for the preparation of compounds of the formula I by selective and inexpensive enzymatic hydrolysis of the compounds of formula II as defined above. The process of the invention, using enzymatic hydrolysis, allows the final product to be obtained under very mild conditions in very high yields and without undesired by-products.

The configuration of the compounds of formulae II and III is [5R,6S,(1R)], in order to obtain the preferred final [5R,6S,(1R)] stereochemistry of the penem nucleus. The starting materials of formula II are known compounds or may be prepared according to known procedures, for example as described in the published U.K. Patent Application GB 2144743-A.

Hydrolytic enzymes suitable for the present process include for example, lipases or proteases which selectively hydrolyze the carboxylic ester of the 2-hydroxymethyl residue (—CH$_2$OCOR) of the compound of formula (II) without affecting other functional groups which may be present. The hydrolytic process can be carried out either by using directly free or immobilized microbial cells which secrete a suitable enzyme or by isolating the specific enzymes which can be used in the free form, immobilized according to known techniques to resins, glass, cellulose or similar substances by ionic or covalent bonds, or grafted to fibres permeable to the substrate, or insolubilized by cross-linkage. Immobilization or insolubilization is advantageous as the same enzyme can be used for many production cycles. Moreover when an immobilized enzyme is used, the recovery of the reaction product is more easy. In fact, if the reaction product is absorbed on the resin at the end of the reaction, it is easily recovered in pure form by simply washing the resin with a suitable solvent.

The use of the enzymes isolated and purified to the desired degree is preferred rather than the raw cellular extract, since the extraction or purification process normally allows a reduction or elimination of the presence of contaminating enzymes which could lower the yields by formation of undesired by-products.

Also enzymatic preparations obtained by extraction of animal organs, such as porcine pancreas, are able to promote hydrolysis of the ester bond between the carbonyl group of an organic acid and the hydroxymethyl group in position 2 of the penem nucleus. Commercially available hydrolytic enzymes can be used in the hydrolytic process such as:

| Enzyme | Origin | Seller |
|---|---|---|
| Pancreatin | Porcine pancreas | UNIBIOS - Trecate (Italy) |
| Steapsin | Porcine pancreas | SIGMA Chem. Co. St. Louis (U.S.A.) |
| Lipase | *Candida cylindracea* | SIGMA Chem. Co. St. Louis (U.S.A.) |
| Lipase | Wheat germ | SIGMA Chem. Co. St. Louis (U.S.A.) |
| Lipase SP 225 | | NOVO Industri (Denmark) |
| Lipase | Rhizopus Delamar | SIGMA Chem. Co. St. Louis (U.S.A.) |
| Lipase | *Chromobacterium viscosum* | TOYO JOZO (Japan) |
| Lipoprotein Lipase | Pseudomonas sp. | TOYOBO (Japan) |
| Protease | *Streptomyces caespitosus* | SIGMA Chem. Co. |
| Protease | Rhizopus sp. | SIGMA Chem. Co. |

The enzymes may be added to an aqueous suspension of from 1 to 100 g/l of the ester formula II, optionally containing small amounts of hydrocarbons, and suitably mildly buffered at different pH values, according to the enzyme used, which are in a range from 5 to 9, preferably from 6 to 8. The reaction may be carried out at a temperature of from 10° C. to 50° C., preferably from 20° C. to 40° C., for 0.5 to 48 hours, operating batchwise or in a column, according to the quantity of the enzyme present in the reaction mixture, and according to the ratio between the quantity of the enzyme in solution or in the immobilized form, and the quantity of substrate present in the reaction mixture. The pH of the reaction mixture is kept constant at the desired value by adding a solution of an alkali hydroxide thereto.

The yields of the reaction carried out under optimal conditions reach values higher than 90%. At the end of the reaction, the reaction product is recovered by conventional methods.

Having generally described this invention, a further understanding can be obtained by reference to certain specific examples which are provided herein for purposes of illustration only and are not intended to be limiting unless otherwise specified.

Preparation A)

Allyl (5R,6S)-2-butyryloxymethyl-6-[1(R)-trimethylsilyloxyethyl]-penem-3-carboxylate A 4.27 g amount of (3S, 4R)-4-butyryloxyacetyl-thio-3-(1(R)-trimethylsilyloxyethyl)-2-azetidinone was dissolved in 40 ml dry toluene. A 700 mg amount of calcium carbonate and 2.2 g of allyloxyoxalylchloride were added to the solution under nitrogen atmosphere at a temperature of 10° C. Triethylamine (2.1 ml) was added dropwise to the mixture, at the same temperature, over a 30 min. period. At the end of the addition, the mixture was stirred for 10 min. at 10° C. Calcium carbonate was removed by filtration and the solution was washed with water, 5% NaHCO$_3$, and then water. After drying over Na$_2$SO$_4$, the solution was concentrated to 20 ml. A 4.7 ml amount of triethylphosphite was added to the concentrate and this mixture was refluxed for 6 h.

The reaction mixture was cooled at 20° C., washed with water (3×10 ml), and dried over Na$_2$SO$_4$.

Evaporation of the solvent gave a crude oil, which was chromatographed on silica gel (ethyl ether/hexane 3:7 v/v) to afford 2.6 g of pure allyl (5R,6S)-2-butyryloxymethyl-6-[1(R)-trimethylsilyloxyethyl]-penem-3-carboxylate (50%).

NMR (300 NHz, CDCl$_3$)—δ(ppm)
0.13 [9H, s, Si(CH$_3$)$_3$]
0.95 (3H, t, OCOCH$_2$CH$_2$$\overline{CH_3}$)
1.25 (3H, d, $\overline{CH_3}$CH)
1.7 (2H, m, OCOCH$_2$$\overline{CH_2}$CH$_3$)
2.3 (2H, t, OCO$\overline{CH_2}$CH$_2$CH$_3$)
3.7 (1H, dd, H-6)
4.2 (1H, m, H-8)
4.7 (2H, m, $\overline{CH_2}$—CH=CH$_2$)
5.2-5.5 (2H, m, CH=$\overline{CH_2}$)
5.05-5.55 (2H, m, $\overline{CH_2}$OCO)
5.55 (1H, d, H-5) - 5.9-6.0 (1H, m, $\overline{CH}$=CH$_2$).

Preparation B)

Allyl (5R,6S)-2-acetyloxymethyl-6-[1(R)-trimethylsilyloxyethyl]-penem-3-carboxylate The preparation was conducted as described in A), starting from (3S, 4R)-4-acetoxyacetylthio-3-(1(R)-trimethylsilyloxyethyl)-2-azetidinone. Allyl (5R,6S)-2-acetyloxymethyl-6-[1(R)-trimethylsilyloxyethyl]-penem-3-carboxylate was obtained as a pure product in an overall yield of 48%.

NMR (300 NHz, CDCl$_3$)—δ4 (ppm)
0.15 (9H, s, Si(CH$_3$)$_3$)
1.28 (3H, d, $\overline{CH_3}$CH)
2.1 (3H, s, CO$\overline{CH_3}$)
3.72 (1H, dd, J=2Hz, 6Hz, H-6)
4.21 (1H, m, H-8)
4.65-4.80 (2H, m, COO$\overline{CH_2}$—CH=)
5.05-5.55 (2H, m, $\overline{CH_2}$OCO)
5.25-5.5 (2H, m, CH=$\overline{CH_2}$)
5.55 (1H, d, J=2Hz, H-5)
5.85-5.60 (1H, m, $\overline{CH}$=CH$_2$).

Preparation C

Allyl (5R,6S)-2-butyryloxymethyl-6-[1(R)-tetrahydropyranyloxyethyl]-penem-3-carboxylate The preparation was conducted as described in A), starting from (3S, 4R)-4-butyryloxyacetylthio-3-[1(R)-tetrahydropyranyloxyethyl]-2-azetidinone. Allyl (5R,6S)-2-burtyryloxymethyl-6-[1(R)-tetrahydropyranyloxyethyl]-penem-3-carboxylate was obtained as a pure product in an overall yield of 45%.

NMR (300 NHz, CDCl$_3$)—δ(ppm)
0.95 (3H, t, J=6.7 Hz,COCH$_2$CH$_2$$\overline{CH_3}$)
1.30-1.37 (3H, m, $\overline{CH_3}$—CH)
1.42-1.90 (6H, m, CH$_2$CH$_2$CH$_2$ of tetrahydropyranyl group)
1.67 (2H, m, COCH$_2$$\overline{CH_2}$CH$_3$)
2.32 (2H, t, OCO$\overline{CH_2}$CH$_2$CH$_3$)
3.4-3.9 (2H, m, OCH$_2$ of tetrahy dropyranyl group)
3.8 (1H, m, H-6)
4.05-4.2 (1H, m, H-8)
4.6-4.85 (3H:COO$\overline{CH_2}$—CH= and CH of tetrahydropyranyl)

5.05-5.5 (2H, m, $\overline{CH_2}OCO$)
5.2-5.42 (2H, m, CH=$\overline{CH_2}$)
5.6 (1H, m, H-5)
5.85-6.0 (1H, m, $\overline{CH}$=CH$_2$).

EXAMPLE 1

A 5 g amount of allyl (5R,6S)-2-butyryloxymethyl-6-[1(R)-trimethylsilyloxyethyl]-penem-3-carboxylate, dissolved in 5ml n-hexane, was added to 300 ml of phosphate buffer 0.05N (pH=7.5). To the mixture was added 25 mg of lipase from Chromobacterium Viscosum and stirred at 30° C. for 4 hours.

The pH was kept at 7.50 by addition of 1N NaOH.

At the end of the reaction, the reaction mixture was extracted with CH$_2$Cl$_2$ (3×100 ml). The organic layer was dried over sodium sulfate and evaporated to give 3.9 g of pure allyl (5R,6S)-2-hydroxymethyl-6-[1(R)-trimethylsilyloxyethyl]-penem-3-carboxylate (93%).

$^1$H—NMR (300 MHz, CDCl$_3$)—δ(ppm)
0.15 (9H, s, Si(CH$_3$)$_3$)
1.32 (3H, d, J=6.5 Hz, $\overline{CH_3}$—CH)
3.75 (1H, dd, J=2Hz, 6.5 Hz; H-6)
3.85 (1H, br, OH)
4.25 (1H, m, H-8)
4.65 (2H, s, $\overline{CH_2}$OH)
4.65-4.95 (2H, m, $\overline{CH_2}$—CH=)
5.25-5.5 (2H, m, CH=$\overline{CH_2}$)
5.60 (1H, d, J=2Hz, H-5)
5.95-6.05 (1H, m, $\overline{CH}$=CH$_2$).

EXAMPLE 2

The reaction was carried out as described in Example 1, except that the enzyme used was Lipoprotein lipase (Toyobo) having an activity of 10 U/mg solid.

The mixture was stirred at 30° C. for 2 hours and the product recovered as described in Example 1, obtaining a yield of 94%.

EXAMPLE 3

A 4.5 g amount of allyl (5R,6S)-2-acetoxymethyl-6-[1(R)-trimethylsilyloxyethyl]-penem-3-carboxylate was added to 300 ml of phosphate buffer 0.05N (pH=7.0). This mixture was added with 25 mg of lipase from *Chromobacterium viscosum* to the buffer solution and the resulting solution was stirred at 30° C. for 5 hours.

The pH was kept at 7.0 by addition of 1N NaOH.

At the end of the reaction, the reaction mixture was extracted with CH$_2$Cl$_2$ (3×100 ml). The extracts were dried over sodium sulfate and evaporated to give allyl (5R,6S)-2-hydroxymethyl-6-[1(R)-trimethylsilyloxyethyl]-penem-3-carboxylate in a yield of 95%.

EXAMPLE 4

The reaction was carried out as described in Example 1, except that the enzyme used was Pancreatin(Unibios; 3.5 g). The mixture was stirred at 30° C. for 20 h (pH=7.5). The product was recovered as described in Example 1, with a yield of 91%.

EXAMPLE 5

The reaction was carried out as described in Example 1, except that the enzyme used was Pancreatin (3.5 g). The mixture was stirred at 30° for 22 h (pH=8.0). At the end of the reaction, the mixture was extracted with CH$_2$Cl$_2$ (3×100 ml). The extracts were concentrated under a reduced pressure and chromatographed on a column of silica gel. Material was eluted with a mixed solvent of hexane-ethyl ether (20:80 v/v). Evaporation of the solvent afforded 1.67 g (40%) of allyl (5R,6S)-2-hydroxymethyl-6-[1(R)-trimethylsilyloxyethyl]-penem-3-carboxylate.

EXAMPLE 6

The reaction was conducted as described in Example 5, except that the enzyme used was lipase from wheat germ (3 g). The mixture was stirred at 25° C. for 30 h (pH=7.5). After chromatographic separation, 3.4g of product (80% yield) was obtained.

EXAMPLE 7

The reaction was conducted as described in Example 5, except that the enzyme used was Protease (from *Rhizopus sp.*, 3 g). The mixture was stirred at 30° C. for 20 h (pH=7.5), affording, after chromatography, 2.9 g (70%) of product.

EXAMPLE 8

A 5 g amount of allyl (5R,6S)-2-butyryloxymethyl-6-[1(R)-tetrahydropyranyloxyethyl]-penem-3carboxylate was added to 300 ml of phosphate buffer 0.05N (pH=7.0). The mixture was added to the buffer solution with 25 mg of lipase from *Chromobacterium viscosum* and the resulting solution was stirred at 30° C. for 4 hours. The pH was kept at 7.0 by addition of 1N NaOH. At the end of the reaction, the reaction mixture was extracted with CH$_2$Cl$_2$ (3×100 ml). The organic layer was dried over sodium sulfate and evaporated to give allyl-(5R,6S)-2-hydroxyethyl-6-[1(R)-tetrahydropyranyloxymethyl]-penem-3-carboxylate with a yield of 94%.

H-NMR (300 MHz, CDCl$_3$)—δ(ppm)
1.3-1.4 (3H, m, $\overline{CH_3}$CH)
1.45-1.9 (6H, m, CH$_2$CH$_2$CH$_2$ of THP group)
3.42-3.92 (2H, m, $\overline{CH_2}$O of THP group)
3.6 (1H,br,OH)
3.8 (1H, m, H-6)
4.05-4.22 (1H, m, H-8)
4.57-4.82(5H:COO$\overline{CH_2}$=; CH$_2$OH; CH of THP group)
5.2-5.45 (2H, m, =$\overline{CH_2}$)
5.61 (1H, m, H-5)
5.85-6.0 (1H, m, CH=).

EXAMPLE 9

A 40 g amount of Amberlite XAD-7 was added to a solution of 100 mg Lipase (from Chromobacterium) in 100 ml of 0.01N phosphate buffer (pH=7.5). The resin mixture was gently stirred overnight at room temperature. Then the resin was filtered and washed with 100 ml of the same buffer. The immobilized enzyme resin was added to a suspension of 20 g of allyl (5R,6S)-2-butyryloxymethyl-6-[1(R)-trimethylsilyloxyethyl]-penem-3-carboxylate in 20 ml hexane and 600 ml of 0.01N phosphate buffer (pH=7.5). The mixture was stirred at 30° C. for 4 hours. The pH was kept at 7.50 by addition of 1N NaOH. At the end of the reaction, the resin containing the enzyme and the reaction product were separated by filtration in vacuo through a glass filter and washed with methylene chloride (3×300 ml). The organic extracts were dried over Na$_2$SO$_4$ and evaporated, affording 15.2g (91%) of product.

The immobilized enzyme resin was washed with phosphate buffer (3×200 ml) and used for 6 production cycles without appreciable loss of activity.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. In a process for preparing the compound of formula I:

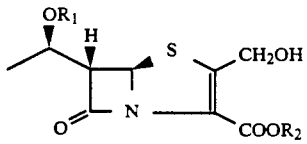

wherein $R_1$ is a p-nitrobenzyloxycarbonyl, trimethylsilyl or pyranyl group and $R_2$ is an allyl, benzyl or a p-nitrobenzyl group, by hydrolyzing a compound of formula II:

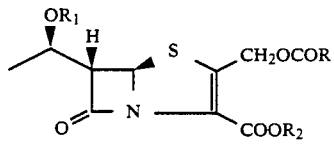

wherein $R_1$ and $R_2$ are as defined above and R is a methyl, ethyl, propyl or butyl group, the improvement comprising: contacting the compound of formula (II) with a lipase which selectively hydrolyzes the —$CH_2OCOR$ group thereof wherein said lipase is obtained from a member of the group consisting of *Candida cylindracea*, wheat germ, *Rhizopus Delamar*, *Chromobacterium*, viscosum and *Pseudomonas specie*.

2. The process according to claim 1, wherein the enzymatic hydrolysis is carried out either in the presence of microbial cells which secrete said lipase or in the presence of isolated enzyme.

3. The process according to claim 2, wherein the microbial cells or the isolated lipase is immobilized on an inert substrate.

4. The process according to claim 2, wherein the microbial cells or the isolated lipase is crosslinked to an inert substrate.

5. The process according to claim 3, wherein the compound of formula I is adsorbed on the inert substrate and then recovered in pure form by washing the substrate with a suitable solvent.

6. The process according to claim 1, wherein the enzymatic hydrolysis is conducted in an aqueous solution, the concentration of the compound of formula II being from 1 to 100 g/l, buffered at a pH from 5 to 9, at the temperature of from 10° to 50° C. for a period of time from 0.5 to 48 hours, optionally in the presence of a small amount of hydrocarbons.

* * * * *